United States Patent
Lee et al.

(10) Patent No.: US 11,176,428 B2
(45) Date of Patent: Nov. 16, 2021

(54) APPARATUS AND METHOD FOR SINOGRAM RESTORATION IN COMPUTED TOMOGRAPHY (CT) USING ADAPTIVE FILTERING WITH DEEP LEARNING (DL)

(71) Applicant: CANON MEDICAL SYSTEMS CORPORATION, Otawara (JP)

(72) Inventors: Tzu-Cheng Lee, Vernon Hills, IL (US); Jian Zhou, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 144 days.

(21) Appl. No.: 16/372,206

(22) Filed: Apr. 1, 2019

(65) Prior Publication Data

US 2020/0311490 A1 Oct. 1, 2020

(51) Int. Cl.
*G06K 9/66* (2006.01)
*G06K 9/40* (2006.01)
(Continued)

(52) U.S. Cl.
CPC .............. *G06K 9/66* (2013.01); *A61B 6/5258* (2013.01); *G01T 1/161* (2013.01); *G06K 9/40* (2013.01);
(Continued)

(58) Field of Classification Search
CPC .......... G06K 9/66; G06K 9/40; A61B 6/5258; G01T 1/161; G06T 7/0014
See application file for complete search history.

(56) References Cited

U.S. PATENT DOCUMENTS 10,685,429 B2 * 6/2020 Mentl .................... G06T 11/008
2010/0092102 A1 * 4/2010 Sun .......................... G06T 5/007
382/260

(Continued)

FOREIGN PATENT DOCUMENTS

EP 3 447 731 A1 2/2019
WO 2017/223560 A1 12/2017

OTHER PUBLICATIONS

Hsieh, J. "Adaptive streak artifact reduction in computed tomography resulting from excessive x-ray photon noise" Medical Physics 25 (11), Nov. 1998; pp. 2139-2147.

(Continued)

*Primary Examiner* — Md K Talukder

(74) *Attorney, Agent, or Firm* — Oblon, McClelland, Maier & Neustadt, L.L.P.

(57) ABSTRACT

A method and apparatus is provided to reduce the noise in medical imaging by training a deep learning (DL) network to select the optimal parameters for a convolution kernel of an adaptive filter that is applied in the data domain. For example, in X-ray computed tomography (CT) the adaptive filter applies smoothing to a sinogram, and the optimal amount of the smoothing and orientation of the kernel (e.g., a bivariate Gaussian) can be determined on a pixel-by-pixel basis by applying a noisy sinogram to the DL network, which outputs the parameters of the filter (e.g., the orientation and variances of the Gaussian kernel). The DL network is trained using a training data set including target data (e.g., the gold standard) and input data. The input data can be sinograms generated by a low-dose CT scan, and the target data generated by a high-dose CT scan.

21 Claims, 9 Drawing Sheets

(51) Int. Cl.
  *G06T 7/00* (2017.01)
  *G01T 1/161* (2006.01)
  *A61B 6/00* (2006.01)
(52) U.S. Cl.
  CPC .. *G06T 7/0014* (2013.01); *G06T 2207/10081* (2013.01); *G06T 2207/10104* (2013.01); *G06T 2207/10116* (2013.01); *G06T 2207/20004* (2013.01); *G06T 2207/20081* (2013.01)

(56) References Cited

U.S. PATENT DOCUMENTS

| | | | | |
|---|---|---|---|---|
| 2013/0051516 | A1* | 2/2013 | Yang | A61B 6/5282 378/4 |
| 2014/0194735 | A1* | 7/2014 | Panin | A61B 6/5258 600/425 |
| 2018/0018757 | A1* | 1/2018 | Suzuki | A61B 6/5205 |
| 2020/0043204 | A1* | 2/2020 | Fu | G06N 3/0454 |
| 2020/0196972 | A1* | 6/2020 | Zhou | A61B 6/482 |
| 2020/0311490 | A1* | 10/2020 | Lee | G06K 9/6256 |
| 2020/0311914 | A1* | 10/2020 | Zaharchuk | G06N 20/10 |

OTHER PUBLICATIONS

Manduca, A. et al. "Projection space denoising with bilateral filtering and CT noise modeling for dose reduction in CT" Medical Physics 36 (11), Nov. 2009; pp. 4911-4919.

Maier, A. et al. "Three-dimensional anisotropic adaptive filtering of projection data for noise reduction in cone beam CT" Medical Physics 38 (11), Nov. 2011; pp. 5896-5909.

Li, T. et al. "Nonlinear Sinogram Smoothing from Low-Dose X-Ray CT" IEEE Transactions on Nuclear Science; vol. 51; No. 5, Oct. 2004; pp. 2505-2513.

La Riviere, P. "Penalized-likelihood sinogram smoothing for low-dose CT" Medical Physics 32 (6), Jun. 2005; pp. 1676-1683.

Zhu, Y. et al. "Noise reduction with low dose CT data based on a modified ROF model" Optics Express vol. 20; No. 16; Jul. 2012; pp. 17987-18004.

Yang, Q. et al. "CT Image Denoising with Perceptive Deep Neural Networks" The 14th International Meeting on Fully Three-Dimensional Image Reconstruction in Radiology and Nuclear Medicine; DOI: 10.12059; Jun. 2017; pp. 858-863.

Kang, E. et al. "A deep convolutional neural network using directional wavelets for low-dose X-ray CT reconstruction" Medical Physics 44 (10), Oct. 2017; pp. e360-e375.

Chen, H. et al. "Low-Dose CT With a Residual Encoder-Decoder Convolutional Neural Network" IEEE Trans Medical Imaging 36 (12), 2017; pp. 2524-2535.

Muhammad Usman Ghani, et al. "Deep Learning Based Sinogram Correction for Metal Artifact Reduction", Society for Imaging Science and Technology, 2018, pp. 472-1 to 472-8.

* cited by examiner

APPARATUS AND METHOD FOR SINOGRAM RESTORATION IN COMPUTED TOMOGRAPHY (CT) USING ADAPTIVE FILTERING WITH DEEP LEARNING (DL)

FIELD

This disclosure relates to reconstruction of medical images in which denoising of the images is performed using a deep-learning network based on feature-aware training, and, more particularly, the denoising and artifact reduction can be performed on medical images including: (i) X-ray computed tomography (CT) images.

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

Medical imaging produces images of the internal members of a patient's body. Examples of medical-imaging modalities include: X-ray radiography, X-ray computed tomography (CT), positron emission tomography (PET), single-photon emission CT (SPECT), fluoroscopy, and angiography. Once the images have been produced, a physician can use the images to diagnose a patient's injuries or diseases X-ray CT systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

X-ray CT has found extensive clinical applications in cancer, heart, and brain imaging. As CT has been increasingly used for a variety of applications including, e.g., cancer screening and pediatric imaging, there has arisen a push to reduce the radiation dose of clinical CT scans to become as low as reasonably achievable. For low-dose CT, the image quality can be degraded by many factors, such as high quanta noise challenge scanning geometry.

Although many cutting-edge technologies have been developed during to improve low-dose CT image quality, better methods (e.g., faster, more robust, and/or improved noise suppression) are desired to further suppress noise and generate clinical image quality with lower X-ray doses.

BRIEF DESCRIPTION OF THE DRAWINGS

A more complete understanding of this disclosure is provided by reference to the following detailed description when considered in connection with the accompanying drawings, wherein.

DETAILED DESCRIPTION

Figure 1:
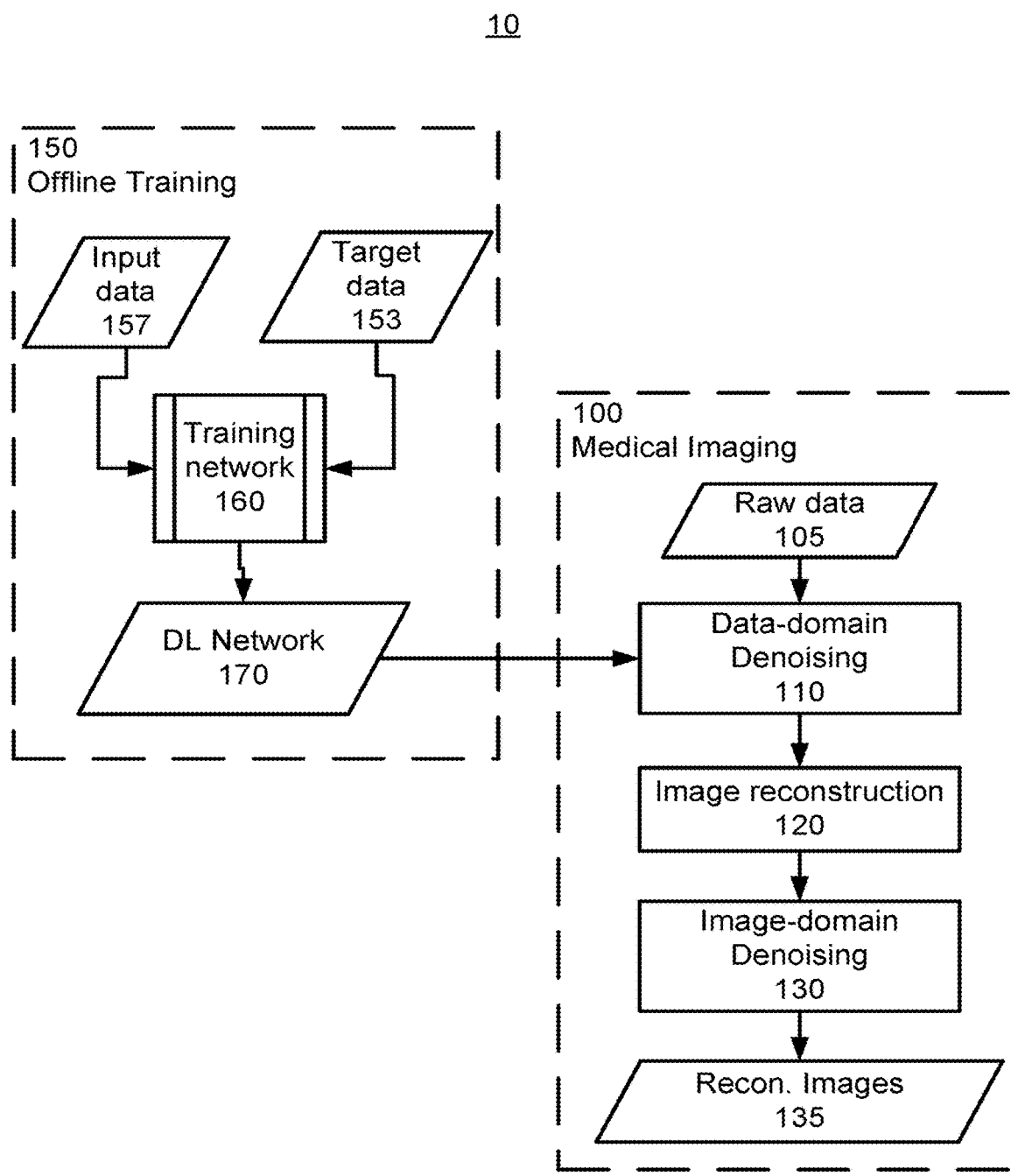
FIG. 1 shows a flow diagram of a method of training a deep learning (DL) network and then using the DL network to denoise computed tomography (CT) data in the projection domain and then reconstruct an image from the denoised data, according to one implementation.

As discussed above, better methods for noise suppression are desirable for many reasons, including that better noise suppression can enable clinical image quality at lower radiation doses. Additionally, methods for noise suppression can be improved by making them faster or more robust. The methods described herein provide improved performance for noise suppression by performing data-domain sinogram restoration using denoising filter that is specifically tailored to the given projection data. The denoising filter is specifically tailored to the given projection data using a deep learning network to determine for the given projection data the optimal parameters for a kernel of the denoising filter.

Accordingly, the methods described herein can advantageously reduce computational time, hardware costs, and improve image quality for medical images, such as computed tomography (CT) images. Further, the examples provided herein use CT imaging as an illustrative non-limiting example. However, and the methods described herein can be used with other medical imaging modalities such as PET and SPECT, etc. by adapting the framework proposed herein. Accordingly, the discussion herein discloses and describes non-limiting examples of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

As discussed above, the methods described herein use a DL network (which can also be referred to as a neural network or an artificial neural network) that has been trained to select the parameters of a kernel of a denoising filter to optimize the sinogram restoration/denoising. Thus, the denoising filter is selectively tailored to denoise the particular projection data. These kernel parameters selected by a DL network can result in improved performance relative to related methods that also use data-domain denoising techniques to improve the image quality of CT reconstructed images.

Instead of using a DL network, related methods use either adaptive filtering or statistics-based mean estimation to select the kernel parameters. Compared to the methods described herein, these related methods have their respective shortcomings/challenges. For example, statistical mean estimation methods require multiple iterations to obtain a converged solution, which can be computational intensive and time consuming. Further, some of model parameters related to the mean estimation (e.g., parameter to control regularization strength) can only be selected manually, requiring user input.

Further, adaptive selection of the kernel parameters can be also be challenging. For example, data-domain adaptive filtering method uses a filter having a small kernel (e.g., Gaussian function with a small width/variance). The kernel is locally adapted to the data to smooth out noise. The adaptive filters can be chosen from known kernel functions (e.g., triangle function and Gaussian function) with parameters such as the variance of the kernel that are chosen empirically. Accordingly, the optimal kernel design and parameter selection for adaptive filtering can be difficult, especially in practical situations when the scan conditions are sometimes poor.

The methods described herein address the above-noted challenges with related methods by training a DL network to select the optimal kernel parameters for an adaptive filtering framework to perform sinogram restoration/denoising in the data domain.

To illustrate, the methods described herein can use a smoothing filter to denoise projection/emission data in the data domain (as opposed to denoising in the image domain). A neural network can be trained to determine the parameters for a kernel of the smoothing filter by applying a sinogram to the neural network as an input. Further, the smoothing filtering can be performed by convolving the sinogram with a Gaussian kernel, the parameters of the Gaussian kernel (i.e., the width/variance of the Gaussian) that are determined by the neural network can be vary as a function of position/pixel within the sinogram.

Using a DL network to determine the kernel parameter for an adaptive smoothing filter provides several advantages over the above-noted related methods.

First, the DL network can learn optimal strategies for adaptively filtering in the data domain by training on actual data to minimize a loss function. This helps to reduce the effort of manual kernel selection which is often challenging in the related adaptive filtering method. Compared to ad-hoc or manually tuned adaptive filtering methods, the DL network can produce better performance (e.g., achieve a more favorable tradeoff between noise reduction and resolution) by learning patterns in the data that are too subtle or counterintuitive to discover empirically without machine learning.

Second, the methods described herein are more flexible and robust than the related methods because the method for training the DL network is independent of a particular type or source of noise.

Third, different loss function can be selected to achieve different denoising effects. For example, the loss function can be the $\ell_p$-norm of the difference between the target data and the result of applying the input data to the DL network. Different values of "p" in the $\ell_p$-norm can be used to emphasize different aspects of the noise. Further, a weighting mask (e.g., based on the attenuation coefficient of signal intensity) can be applied on a pixel-by-pixel basis to the difference between the target data and the result generated from the input data. In certain implementations, rather than minimizing an $\ell_p$-norm of the difference between the target data and the result from the input data, the loss function can represent a similarity (e.g., using a peak signal-to-noise ratio (PSNR) or a structural similarity (SSIM) index).

Fourth, the DL network can be fast computationally because only a small number of parameters are required to define the kernel of the smoothing function.

Herein the phrase "data domain" is used to distinguish CT projection data from image data (i.e., reconstructed images) generated via CT reconstruction, which is in the "image domain." That is, the "data domain" is the projection data prior to reconstruction, and the "image domain" is the image data after reconstruction. The data domain can also be referred to as the "projection domain" and the "sinogram domain." In general, the projection in the data domain has three dimensions, which can be referred to as view, channel, and segment, respectively. The dimensions channel and segment correspond to the two directions/axes of the two-dimensional X-ray detector array, and the dimension view corresponds to the projection angle or projection view at which a projection image is acquired. The denoising/smoothing filter can be a three-dimensional (3D) filter corresponding to all three dimensions of the data domain, but often the denoising/smoothing filter can be a two-dimensional (2D) filter (e.g., a 2D convolution with a 2D Gaussian kernel). When the denoising/smoothing filter is a 2D filter, the filter is applied to only two of the three dimensions (e.g., to only the view and channel dimensions or to only the channel and segment dimensions).

The term "data domain" is used instead of "sinogram domain" to avoid the erroneous interpretation that, because a sinogram plot often includes the view dimension, the denoising/smoothing filter must be applied to a set of dimensions that includes the view dimension. Rather, the term "sinogram" is not limited to projection data that includes the view dimension, but sinogram data can include, e.g., a projection image at a 2D single view having only segment and channel dimensions. Accordingly, the data-domain denoising methods described herein are not limited to any particular combination of dimensions, but cover all possible permutations of dimensions for the denoising/smoothing filter (e.g., the denoising/smoothing filter can be either a 2D or 3D filter applied to any combination of the view, channel, and segment dimensions). For example, the denoising/smoothing filter can being applied to (i) the view and channel dimensions, (ii) the channel and segment dimensions, (iii) the view and segment dimensions, and (iv) the view, channel, and segment dimensions. Further, the methods described herein include the implementation in which a first denoising/smoothing filter is applied to a first set of dimensions (e.g., the view and channel dimensions) to generate once-filtered data, and then a second denoising/smoothing filter is applied to the once-filtered data along a second set of dimensions (e.g., the channel and segment dimensions) to generate twice-filtered data.

X-ray CT is used as the primary illustrative example herein, but the methods described are also applicable to PET, SPECT, and fluoroscopy, for example. Although, the illustrative example describes applying a smoothing filter to sinograms from X-ray CT, the smoothing/denoising could also be applied to projection data from X-ray fluoroscopy acquired at a single view angle because the smoothing/denoising is applied in the data domain (i.e., not in the image domain). That is, smoothing/denoising can be applied in the data domain independent of whether the denoised projection data is later used for CT reconstruction.

Further, the filter applied in the data domain is not limited to being a smoothing filter. For example, the filter could include a convolution kernel for edge enhancement or for artifact suppression. In certain implementations, the convolution kernel and the parameters of the convolution kernel can be selected to achieve one or more of denoising, edge enhancement, and artifact suppression. Nevertheless, the methods described herein are illustrated without loss of generality using the non-limiting example of a smoothing/denoising filter to denoise the projection data in the sinogram domain.

Referring now to the drawings, wherein like reference numerals designate identical or corresponding parts throughout the several views, FIG. 1 shows a flow diagram for a non-limiting example of a method that trains and uses a DL neural network 170 to perform data-domain corrections of CT projection data (e.g., sinogram restoration, denoising, smoothing, and/or artifact correction). Method 10, as illustrated in FIG. 1, uses DL network 170 to learn how to denoise raw data 105, and then reconstructs a CT image from the denoised data. Method 10 includes two parts: (i) an offline training process 150 and (ii) a medical imaging process 100. That is, process 150 trains the DL network 170, and process 100 uses the trained DL network 170 to denoise projection data in the data domain, thereby generating high-quality images 135 with reduced noise and artifacts.

In certain implementations, the network 170 includes a convolutional neural network (CNN) in which series of convolution (conv), batch normalization (BN), and rectified linear unit (ReLu) network layers are performed.

The network 170 is trained using process 160. In process 160, a loss function is used to iteratively adjust/optimize parameters of the DL network 170 (e.g., the parameters of the DL network 170 can include weighting coefficients connecting network layers, and activation functions/potentials of nodes within the layers). The optimization of the network parameters continues until stopping criteria are satisfied (e.g., a stopping criterion can be whether the value of the loss function converged to a predefined threshold) to generate the trained network 170.

The loss function compares target data 153 to an output acquired using the input data 157 and a current version of the DL network 170. For example, the input data can include noisy projection data in the data domain for respective CT scans, and the target data can include low-noise (i.e., less noise than the input data) projection data in the data domain for the same respective CT scans. For example, each noisy dataset for a given scan can form a pair with a corresponding noise-reduced dataset for the given scan. In one implementation, the noisy dataset is generated using a low-dose scan, and the noise-reduced dataset is generated using a high-dose scan. These scans can be performed on a phantom, for example. Herein, to avoid the ambiguity of using the mass noun "data," when referring to the projection data for a given CT scan, the term "sinogram" is used herein to indicate the unit of projection data in the data domain corresponding to a complete CT scan.

Applying a noisy sinogram from the input data to the current version of the DL network 170 generates an output from the network that is supposed to be a denoised version of the noisy sinogram (i.e., a denoised sinogram). The DL network 170 is trained by iteratively adjusting the network coefficients in the DL network 170 to minimize the difference between the denoised sinogram output from the network 170 and the noise-reduced sinogram from the target data 153. The training of the network 170 is determined to be complete when the difference is minimized between network output and the target data, and whether or not the difference has been sufficiently minimized is based on one or more predetermined stopping criteria of process 160. Once the stopping criteria have been satisfied, the trained network 170 can then be stored and then later recalled to be used in the medical imaging process 100.

In method 10, a loss function is used to iteratively adjust network coefficients (e.g., weights and biases of convolutional and pooling layers) of the DL network 170 until stopping criteria are satisfied (e.g., convergence of the parameters to a predefined threshold) to generate the trained network 170. The loss function compares high-quality data 153 to results of a current version of the DL network 170 to which input data 157 is applied.

As discussed above, CT image reconstruction is only one non-limiting illustrative example. Another example is positron emission tomography (PET) imaging. In the case PET imaging, sinograms can be generated for positron emission data, and sinogram denoising/restoration can be applied to the positron emission data using method 10. For example, method 10 includes training a DL network 170 and applying a low-quality (e.g., noisy) PET sinogram (i.e., raw data 105) to the trained network 170 to generate a high-quality (e.g., denoised) PET sinogram.

In the case of PET imaging, the high- and low-quality data are accumulated over scans having long and short time durations, respectively. In general, the signal-to-noise ratio (SNR) is smaller for sinograms accumulated over shorter time durations. Accordingly, the target data 153 (e.g., high-quality sinograms) can be generated using all of the coincidence counts from a full-length PET scan to generate the highest possible SNR for the sinogram. On the other hand, the low-quality input data 157 can be generated using a partial subset of coincidence counts selected from the full dataset (e.g., using the data from only half of the full-length PET scan), resulting in a noisier sinogram (e.g., a $\sqrt{2}$ smaller SNR).

Returning to FIG. 1, process 100 is performed by obtaining raw data, e.g., by performing a CT scan to generate CT projections at a series of view angles (i.e., a noisy sinogram). For example, the sinogram can be performed using a low-dose CT scan to generate the raw data 105.

In step 110 of process 100, the raw data 105 is denoised by applying the raw data 105 to the trained DL network 170. The DL network 170 then outputs a denoised sinogram.

In step 120 of process 100, a CT image is reconstructed from the denoised sinogram. Various methods can be used to reconstruct CT images from projection data, including filtered back-projection (FBP) and statistical iterative reconstruction (IR) algorithms. In addition to FBP, other analytical methods can be used such as the Feldkamp Davis Kress (FDK) method Adaptive Iterative Dose Reduction 3D (AIDR 3D) method. Compared to FBP reconstruction methods, IR methods can provide improved image quality at reduced radiation doses.

One IR method performs unconstrained (or constrained) optimization to find the argument p that minimizes the expression $$\underset{p}{\operatorname{argmin}}\{\|Ap - \ell\|_W^2 + \beta U(p)\},$$

wherein $\ell$ is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $\ell_i$. The data-fidelity term $\|Ap-\ell\|_w^2$ is minimized when the forward projection A of the reconstructed image p provides a good approximation to all measured projection images $\ell$. Thus, the data fidelity term is directed to solving the system matrix equation $Ap=\ell$, which expresses the Radon transform (i.e., projections) of various rays from a source through an object OBJ in the space represented by p to X-ray detectors generating the values of $\ell$ (e.g., X-ray projections through the three-dimensional object OBJ onto a two-dimensional projection image $\ell$).

The notation $\|g\|_w^2$ signifies a weighted inner product of the form $g^T W g$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

The function U(p) is a regularization term, and this term is directed at imposing one or more constraints (e.g., a total variation (TV) minimization constraint) which often have the effect of smoothing or denoising the reconstructed image. The value β is a regularization parameter is a value that weights the relative contributions of the data fidelity term and the regularization term.

In step 130 of process 100, additional image-domain denoising is performed. This step is optional, and can be omitted in some implementations.

Example denoising methods include linear smoothing filters, anisotropic diffusion, non-local means, or nonlinear filters. Linear smoothing filters remove noise by convolving the original image with a convolution kernel that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, the reconstructed image 135 is generated, and the reconstructed image 135 can be displayed to a used or stored for later use.

Figure 2:
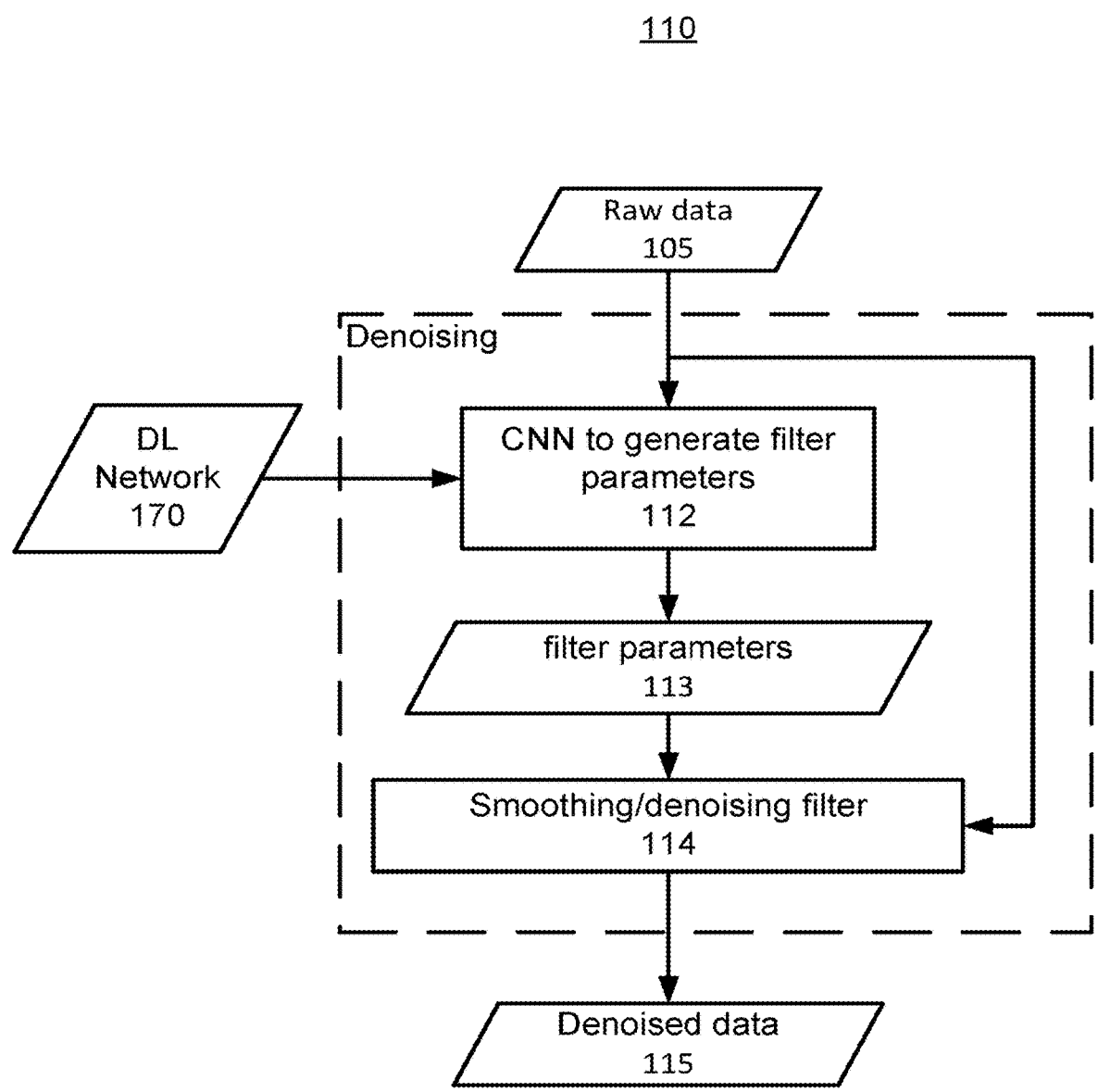
FIG. 2 shows a flow diagram of the process to denoise the projection domain data using the DL network, according to one implementation.

FIG. 2 show a flow diagram for a non-limiting example of step 110. The smoothing is performed in step 114, which uses a smoothing filter to remove noise by convolving the raw data with a kernel of a low-pass filter (e.g., a Gaussian).

The shape of the kernel is not limited to a Gaussian shape, but can be any shape (triangle, square, Blackman-Harris, Dolph-Chebyshev, Hann, Hamming, or other window shape). Further, the kernel does not have to be isotropic, but can be anisotropic. Further, the kernel can by dynamic as a function of position. That is, the kernel can adapt to the local features of the raw data 105. The DL network 170 is used to determine the filter parameters 113 that define the shape of the smoothing filter applied in step 114.

For example, if the smoothing filter is a bivariate Gaussian, then the filter can be defined by three values: a first and second variance and a rotation angle. Further, if the smoothing filter adapts as a function of position, then these three values can vary as a function of position within the raw data 105.

In another example, if the smoothing filter is an isotropic Gaussian, then the filter can be defined by one value: the variance of the Gaussian. And if the smoothing filter adapts as a function of position, then the variance of the Gaussian can vary as a function of position within the raw data 105.

By applying the raw data 105 to the network 170, optimal filter parameters 113 can be determined as a function of position within the raw data 105. For example, a narrower kernel can be desirable in regions of greater signal to preserve resolution and the noise is already reduced in these regions. Further, sinograms can exhibit long skinny regions in certain applications, and it might be desirable to have greater smoothing along the long direction of a ridge than along the narrow direction of the ridge. These are the types of characteristics that the DL network 170 through being trained in process 100.

In general, the raw data 105 can be either pre-log data (i.e., proportional to the intensity of the X-ray radiation) or post-log data (i.e., proportional to the X-ray attenuation coefficient by taking the logarithm of the X-ray intensity). Applying the raw data 105 to the DL network 170 generate filter parameters, making the smoothing filter adaptive to the particular content of the raw data 105 (e.g., a spatially-varying rotation angle and variances). Then in step 114, the parameters generated by the DL network 170 are used to perform adaptive filtering on the raw data 105, generating a restored/de-noised version of the raw data 105.

In certain implementations, the DL network 170 used in step 112 is a convolution neural network (CNN). The CNN can be a network that directly generates local small sized filters, e.g., $$y_i = \sum_{j \in \text{Neighbor of } i} w_{ij} x_j$$

wherein with $w_{ij}$ is the filter on the ith pixel.

In certain implementations, the training data includes input data 157 acquired via a low-dose scan and target data 153 acquired via a high-dose scan (i.e., a high-dose scan being any scan that uses a greater dose than the low-dose scan). Then the raw data 105 is acquired using a low-dose scan similar to that used to generate the input data 157.

In certain implementations, the DL network 170 is a network that generates kernel parameters for a Gaussian kernel; the kernel parameter defining the variances and orientation angle based on the training using the training data. That is, a parametric filter is used (e.g., the Gaussian kernel), and filtering is performed according to the parameters determined by applying the raw data 105 to the DL network 170.

In certain implementations, the target data 153 is higher quality raw data or a sinogram (e.g., from a high dose scan).

Now a more detailed description of training a DL network is provided (e.g., process 160). This description is illustrated using the example of the target data 153 being the noise-reduced sinograms and the input data 157 being noisy sinograms.

Figure 3:
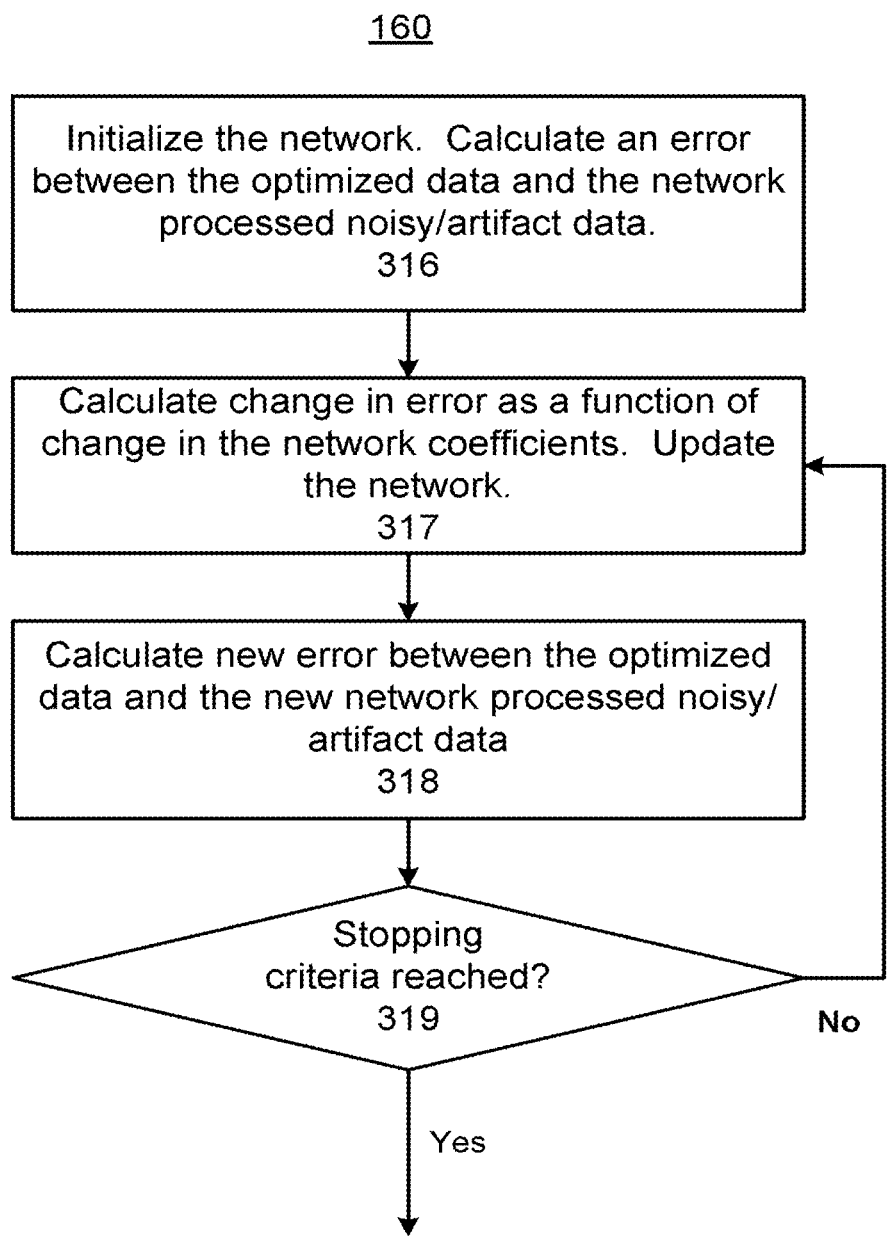
FIG. 3 shows a flow diagram of the process to train the DL network by iteratively adjusting coefficients of the DL network to optimize a loss-error function, according to one implementation.

FIG. 3 shows a flow diagram of one implementation of the training process 160. In process 160, input data 157 (e.g., noisy sinograms) and target data 153 (e.g., noise-reduced sinograms) are used as training data to train a DL network 170, resulting in the DL network 170 being output from step 319 of process 160. The offline DL training process 160 trains the DL network 170 using a large number of input sinograms 157 that are paired with corresponding target sinograms 153 to train the DL network 170 to produce denoised sinograms resembling the target sinograms 153 from the input sinograms 157.

In process 160, a set of training data is obtained, and the network 170 is iteratively updated to reduce the error (e.g., the value produced by a loss function). The DL network infers the mapping implied by the training data, and the cost function produces an error value related to the mismatch between the target sinograms 153 and the result produced by applying a current incarnation of the DL network 170 to the input sinograms 157. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a (stochastic) gradient descent method.

In step 316 of process 160, an initial guess is generated for the coefficients of the DL network 170. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 316 through 319 of process 160 provide a non-limiting example of an optimization method for training the DL network 170.

An error is calculated (e.g., using a loss function or a cost function) to represent a measure of the difference (e.g., a distance measure) between the target sinograms 153 (i.e., ground truth) and input sinograms 157 after applying a current version of the network 170. The error can be calculated using any known cost function or distance measure between the image data, including those cost functions described above. Further, in certain implementations the error/loss function can be calculated using one or more of a hinge loss and a cross-entropy loss.

In certain implementations, the network 170 is trained using backpropagation. Backpropagation can be used for training neural networks and is used in conjunction with gradient descent optimization methods. During a forward pass, the algorithm computes the network's predictions based on the current parameters Θ. These predictions are then input into the loss function, by which they are compared to the corresponding ground truth labels (i.e., the high-quality data 153). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

In certain implementations, the image processing in steps 112 and 114 are considered as being the DL network for backpropagation. However, only the weighting coefficients in the CNN implemented in step 112 are allowed to be changed. That is, the weighting coefficients in the CNN can be adjusted to generate better filter parameters 113, but the only changes to step 114 result from changes in filter parameters 113, which originate outside of step 114. Step 114 itself remains fixed and there are no changes internal to step 114. In this sense the entirety of steps 112 and 114 can be considered as the DL network, even though only the weighting coefficients in the CNN of step 112 are being adjusted by the training process.

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 3, step 317 of process 160 determines a change in the error as a function of the change in the network can be calculated (e.g., an error gradient), and this change in the error can be used to select a direction and step size for a subsequent change to the weights/coefficients of the DL network 170. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 317 of process 160, a new set of coefficients are determined for the DL network 170. For example, the weights/coefficients can be updated using the changed calculated in step 317, as in a gradient descent optimization method or an over-relaxation acceleration method.

In step 318 of process 160, a new error value is calculated using the updated weights/coefficients of the DL network 170.

In step 319, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 160 will continue back to the start of the iterative loop by returning and repeating step 317 using the new weights and coefficients (the iterative loop includes steps 317, 318, and 319). When the stopping criteria are satisfied the training process performed in process 160 is completed.

FIGS. 5A and 5B show various examples of the interconnections between layers in the DL network 170. The DL network 170 can include fully connected, convolutional, and the pooling layer, all of which are explained below. In certain preferred implementations of the DL network 170, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 170 can also incorporate batch normalization, as also exemplified in the first and second examples discussed above.

Figure 4A:
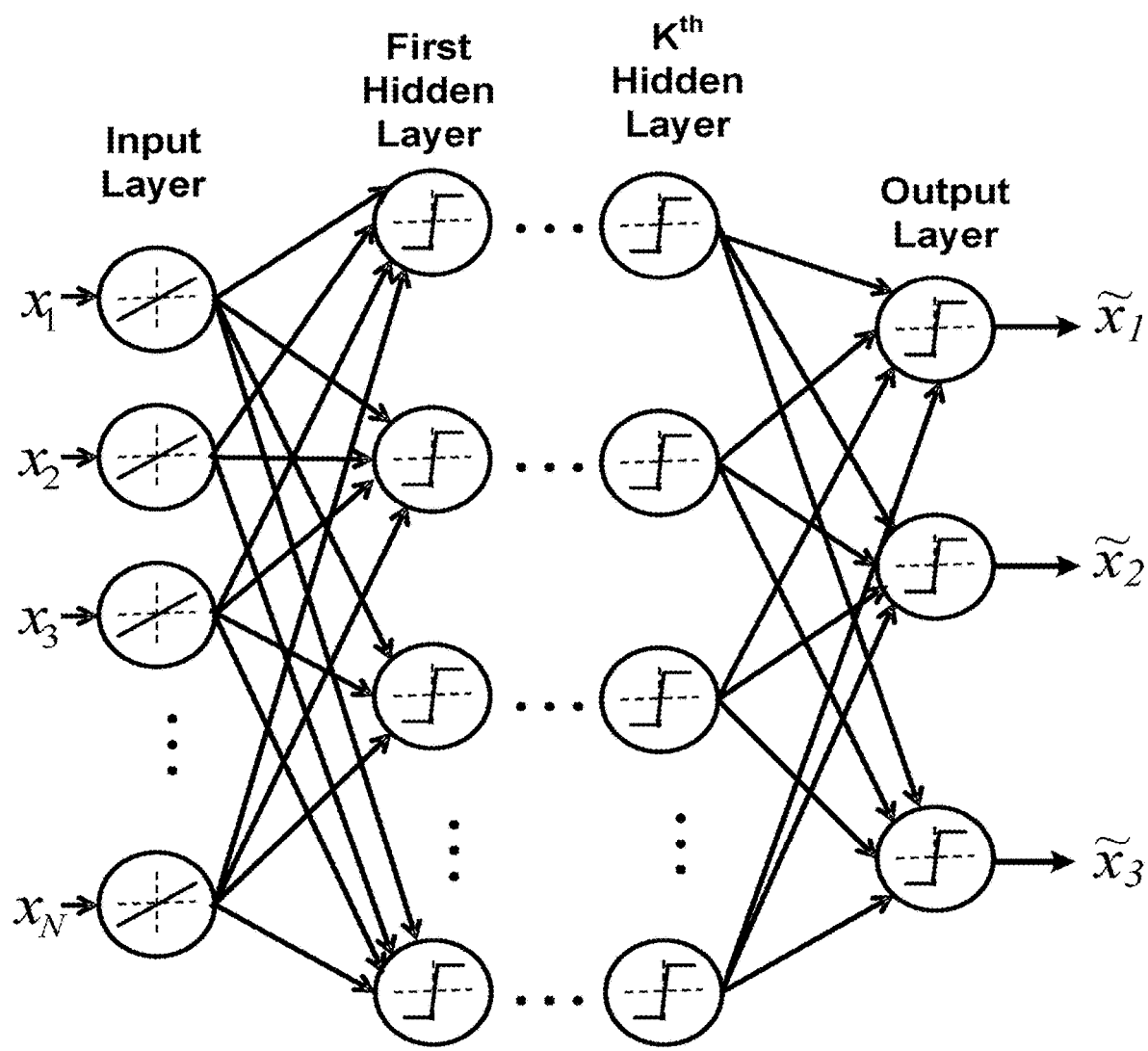
FIG. 4A shows an example of a DL network, according to one implementation.

FIG. 4A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANN s make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 4A. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 4A (and similarly in FIG. 4B), the neurons (i.e., nodes) are depicted by circles around a threshold function. For the non-limiting example shown in FIG. 4A, the inputs are depicted as circles around a linear function, and the arrows indicate directed connections between neurons. In certain implementations, the DL network 170 is a feedforward network.

Figure 4B:
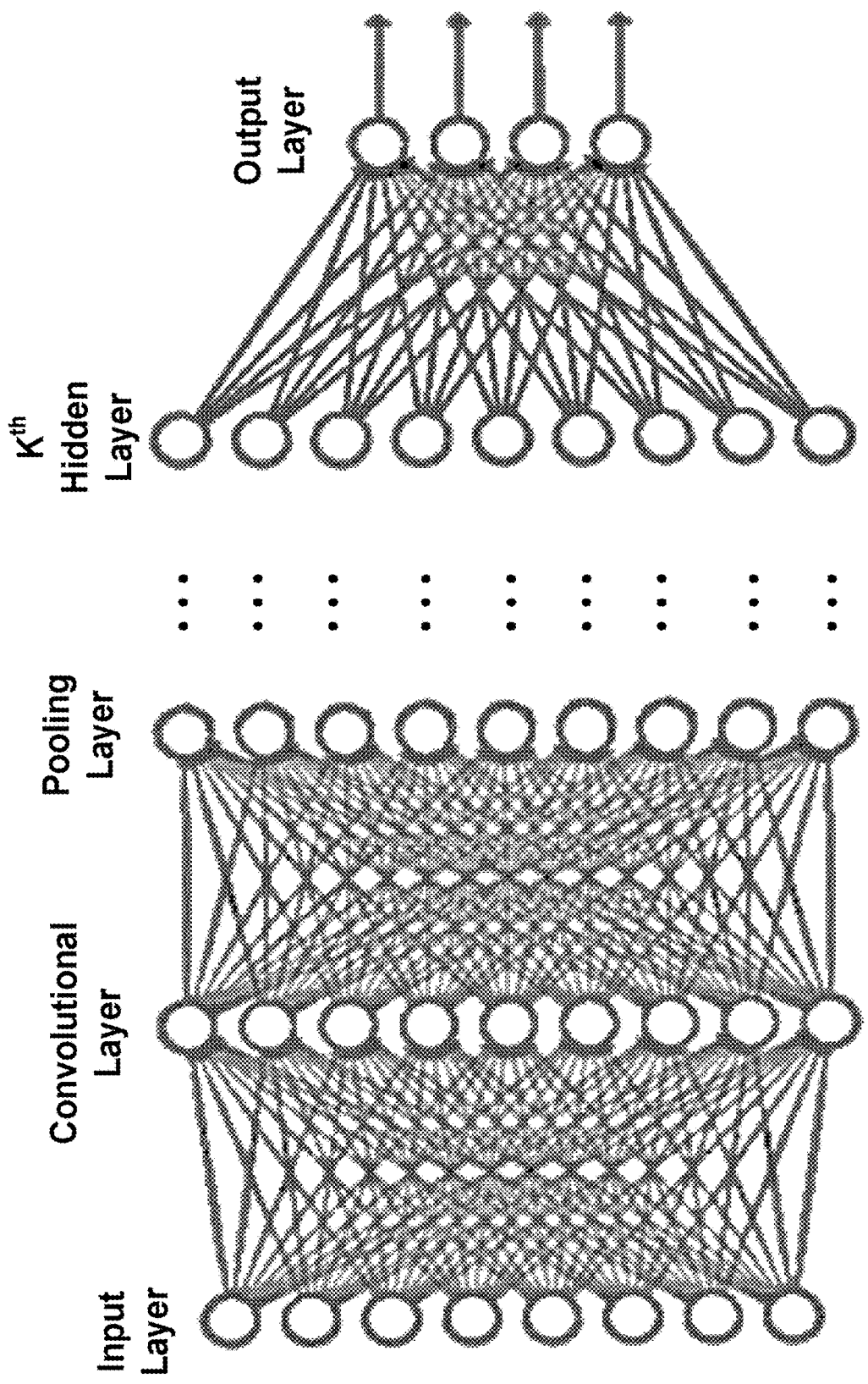
FIG. 4B shows an example of a type of DL network referred to as a convolutional neural network (CNN), according to one implementation.

FIG. 4B shows a non-limiting example in which the DL network 170 is a convolutional neural network (CNN). CNNs are type of ANN that has beneficial properties for image processing, and, therefore, have specially relevancy for the applications of image denoising. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

Figure 5:
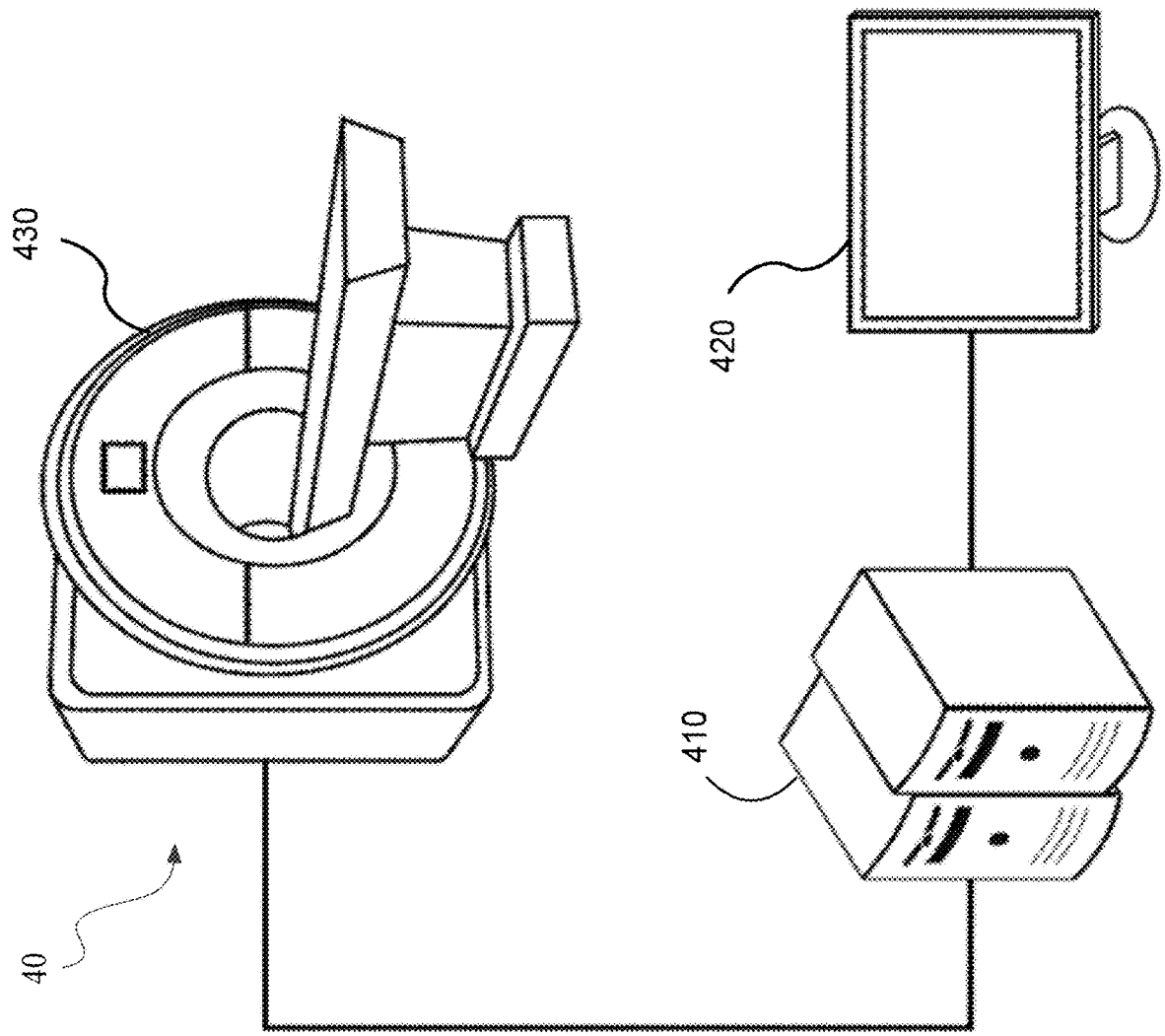
FIG. 5 shows diagram of a medical imaging system, according to one implementation.

FIG. 5 illustrates an example embodiment of a medical-imaging system 40. The medical-imaging system 40 includes at least one scanning device 430; one or more image-generation devices 410, each of which is a specially-configured computing device (e.g., a specially-configured desktop computer, a specially-configured laptop computer, a specially-configured server); and a display device 420.

The scanning device 430 is configured to acquire scan data by scanning a region (e.g., area, volume, or slice) of an object (e.g., a patient). The scanning modality may be, for example, computed tomography (CT), positron emission tomography (PET), and/or single photon emission CT (SPECT). The one or more image-generation devices 410 obtain scan data from the scanning device 430 and generate an image of the region of the object based on the scan data. After the one or more image-generation devices 410 generate the image, the one or more image-generation devices 410 send the image to the display device 420, which displays the image.

Figure 6:
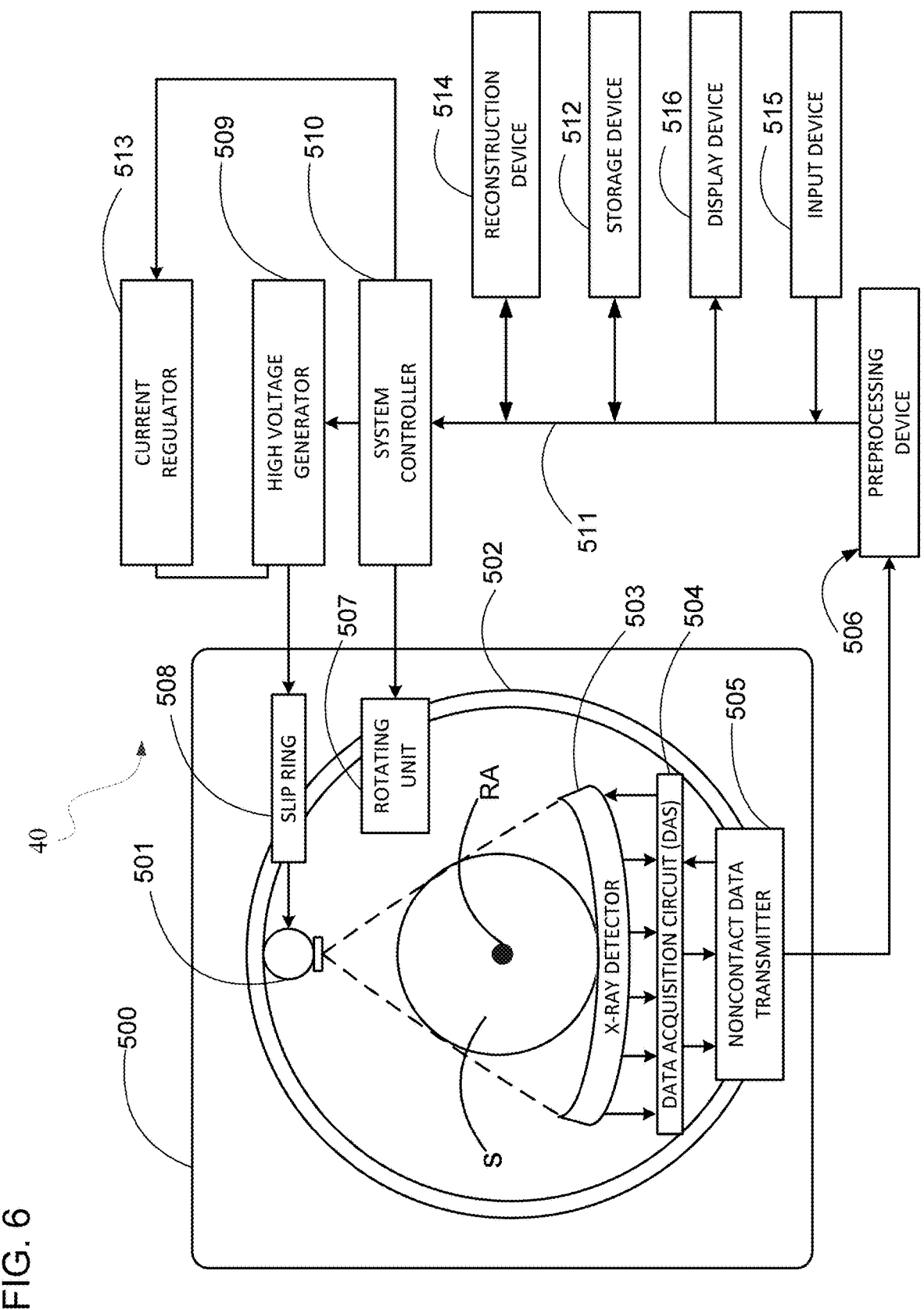
FIG. 6 shows a schematic diagram of an X-ray CT scanner, according to one implementation.
Figure 7A:
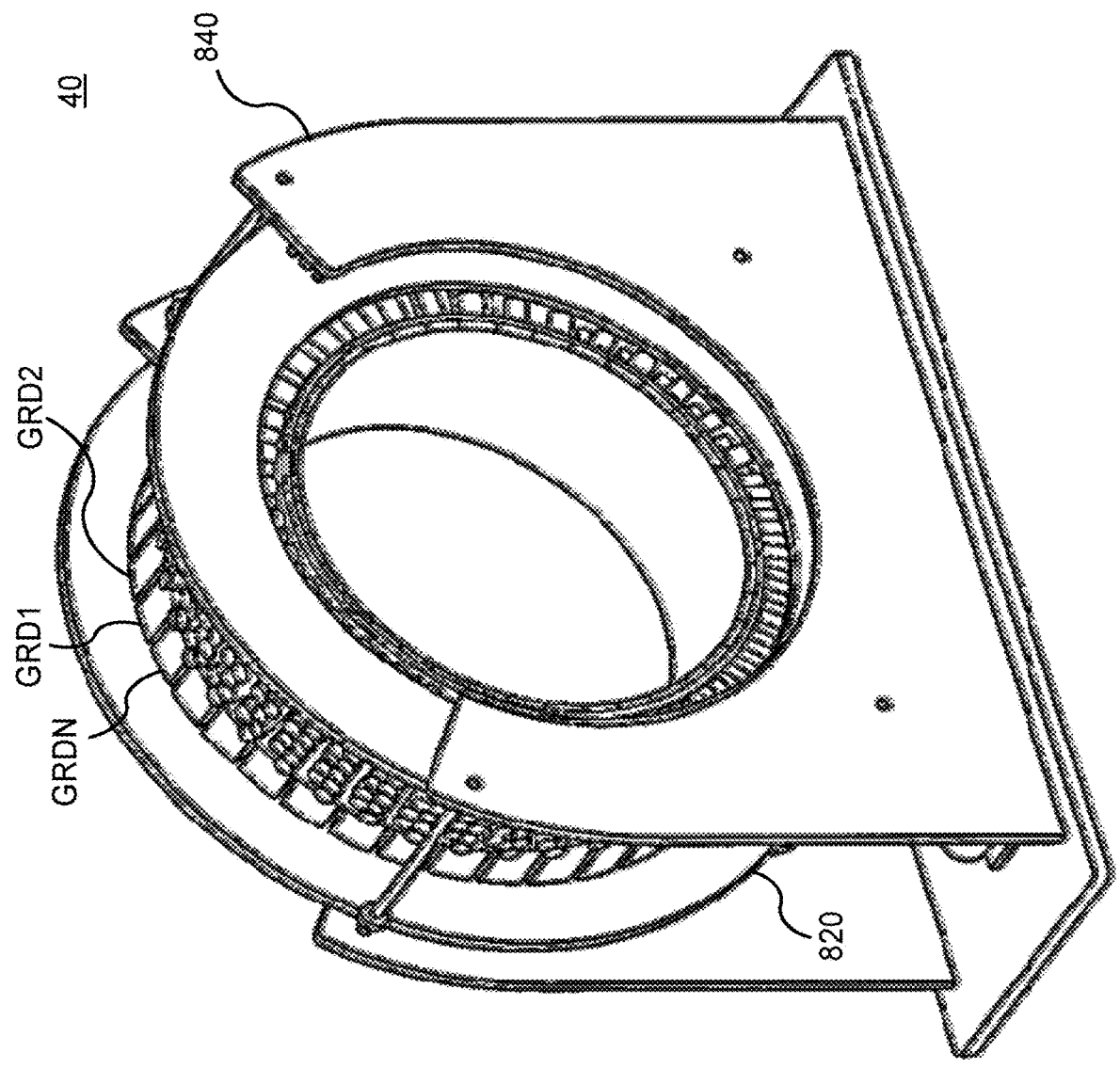
FIG. 7A shows a perspective of a positron emission tomography (PET) scanner, according to one implementation.
Figure 7B:
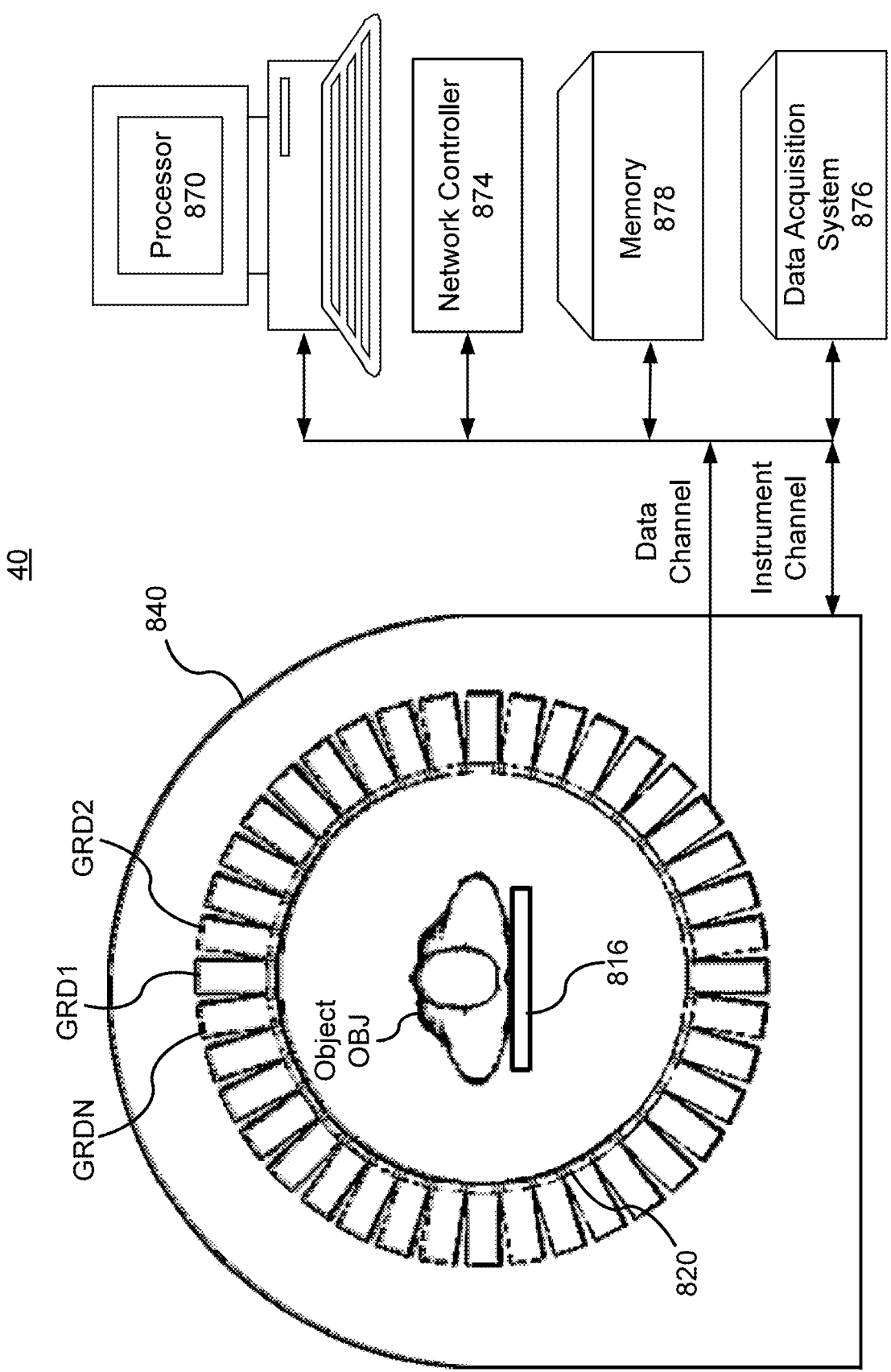
FIG. 7B shows a schematic diagram of the PET scanner, according to one implementation.

FIG. 6 illustrates in implementation in which the medical-imaging system 40 includes a CT scanner. As shown in FIG. 7, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal.

The above-described data is sent to a preprocessing circuitry 506, which is housed in a console outside the radiography gantry 500 through a non-contact data transmitter 505. The preprocessing circuitry 506 performs certain corrections, such as sensitivity correction on the raw data. A storage 512 stores the resultant data, which is also called projection data at a stage immediately before reconstruction processing. The storage 512 is connected to a processing circuitry 510 through a data/control bus 511, together with a reconstruction device 514, input interface 515, and display 516. The processing circuitry 510 controls a current regulator 513 that limits the current to a level sufficient for driving the CT system.

The detectors are rotated and/or fixed with respect to the patient among various generations of the CT scanner systems. In one implementation, the X-ray tube 501 and the X-ray detector 503 are diametrically mounted on the annular frame 502 and are rotated around the object OBJ as the annular frame 502 is rotated about the rotation axis RA.

The storage 512 can store the measurement value representative of the irradiance of the X-rays at the X-ray detector unit 503. Further, the storage 512 can store a dedicated program for executing method 10.

The reconstruction circuitry 514 can execute various steps of method 10. Further, reconstruction circuitry 514 can execute pre-reconstruction processing image processing such as volume rendering processing and image difference processing as needed.

The pre-reconstruction processing of the projection data performed by the preprocessing circuitry 506 can include correcting for detector calibrations, detector nonlinearities, and polar effects, for example.

Post-reconstruction processing performed by the reconstruction circuitry 514 can include filtering and smoothing the image, volume rendering processing, and image difference processing as needed. The image reconstruction process can implement various steps of method 10. The reconstruction circuitry 514 can use the memory to store, e.g., projection data, reconstructed images, calibration data and parameters, and computer programs.

The various circuitry (e.g., the reconstruction circuitry 514 and preprocessing circuitry 506) can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 512 can be non-volatile, such as ROM, EPROM, EEPROM or FLASH memory. The storage 512 can also be volatile, such as static or dynamic RAM, and a processor, such as a microcontroller or microprocessor, can be provided to manage the electronic memory as well as the interaction between the FPGA or CPLD and the memory.

In one implementation, the reconstructed images can be displayed on a display 516. The display 516 can be an LCD display, CRT display, plasma display, OLED, LED or any other display known in the art.

FIGS. 9A and 9B illustrates in implementation in which the medical-imaging system 40 includes a PET scanner that can implement the method 10. The PET scanner includes a number of gamma-ray detectors (GRDs) (e.g., GRD1, GRD2, through GRDN) that are each configured as rectangular detector modules.

Each GRD can include a two-dimensional array of individual detector crystals, which absorb gamma radiation and emit scintillation photons. The scintillation photons can be detected by a two-dimensional array of photomultiplier tubes (PMTs) or silicon photomultipliers (SiPMs). A light guide can be disposed between the array of detector crystals and the photodetectors.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 9B shows a schematic view of a PET scanner having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 9A and 8B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 9B shows an example of the arrangement of the PET scanner, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 9B, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data, pre-reconstruction processing of the detection data, and post-reconstruction processing of the image data, as discussed herein.

The processor 870 can be configured to perform various steps of method 10 described herein and variations thereof. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform various steps of method 10, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMID of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 878 can be a hard disk drive, CD-ROM drive, DVD drive, FLASH drive, RAM, ROM or any other electronic storage known in the art.

The network controller 874, such as an Intel Ethernet PRO network interface card from Intel Corporation of America, can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain radiation data representing an intensity of radiation detected at a plurality of detectors,
acquire a neural network having weighting coefficients that have been trained to determine parameters of a filter, the parameters defining a shape function of a convolution kernel of the filter,
apply the radiation data to the neural network, and in response outputting parameters of the filter based on the radiation data,
filter the radiation data by applying the filter defined by the output parameters from the neural network to generate filtered radiation data, and
reconstruct an image from the filtered radiation data.

2. The apparatus according to claim 1, wherein the circuitry is further configured to obtain the radiation data, wherein the radiation data is a sinogram acquired by generating X-ray projection images at a series of projection views in which an angle between an X-ray source and the plurality of detectors is rotated relative to an image subject, and denoising the sinogram by applying the filter defined by the output parameters from the neural network generates a denoised sinogram, wherein the filter is applied to a three-dimensional volume of the sinogram or to two-dimensional slices of the sinogram, which include a segment dimension and a channel dimension, a view dimension and the channel dimension, and/or the segment dimension and a view dimension.

3. The apparatus according to claim 1, wherein the circuitry is further configured to obtain the radiation data, wherein the radiation data is one of X-ray computed tomography (CT) data, X-ray fluoroscopy data, gamma-ray positron emission tomography (PET), and single-photon emission CT data (SPECT).

4. The apparatus according to claim 2, wherein the circuitry is further configured to reconstruct a computed tomography (CT) image from the denoised sinogram using an analytical reconstruction method.

5. The apparatus according to claim 1, wherein the circuitry is further configured to filter the radiation data, wherein the filter is a smoothing filter, and filtering the radiation data denoises the radiation data.

6. The apparatus according to claim 5, wherein the circuitry is further configured to denoise the radiation data by applying the smoothing filter, wherein the shape function of the smoothing filter is a multi-variate, low-pass-filter kernel and the parameters of the smoothing filter comprise values defining widths and an orientation of the multi-variate, low-pass-filter kernel, and the values comprising the parameters vary as a function of pixel position within the radiation data.

7. The apparatus according to claim 6, wherein the circuitry is further configured to denoise the radiation data by applying the smoothing filter, wherein the multi-variate, low-pass-filter kernel is a multi-variate Gaussian.

8. The apparatus according to claim 1, wherein the circuitry is further configured to filter the radiation data by applying the filter, wherein the filter is a two-dimensional filter applied to two-dimensional slices of the radiation data along a segment dimension and a channel dimension, a view dimension and the channel dimension, or the view dimension and the segment dimension.

9. The apparatus according to claim 2, wherein the circuitry is further configured to acquire the neural network, wherein the weighting coefficients have been trained using training data that includes input data and target data, the input data comprising first training sinograms acquired using a first radiation dose, and the target data comprising second training sinograms using a second radiation dose that is greater than the first radiation dose.

10. The apparatus according to claim 2, wherein the circuitry is further configured to
obtain a training dataset comprising input sinograms paired with respective target sinograms, the input sinograms exhibiting greater noise than the corresponding target sinograms in the respective pairs,
use the neural network to filter one of the input sinograms by
applying the one of the input sinograms to the neural network and in response outputting parameters of the filter, and
denoising the one of the input sinograms by applying, to the one of the input sinograms, the filter defined by the parameters output from the neural network, and thereby generating a filtered sinogram, and
train the neural network iteratively adjusting the weighting coefficients to minimize a value of a loss function, the loss function measuring a disagreement between the respective target sinograms and the filtered sinograms corresponding to the input sinograms.

11. The apparatus according to claim 10, wherein the circuitry is further configured to train the neural network wherein the loss function includes a peak signal to noise ratio, a structural similarity index, and/or an $l_p$-norm of a difference between the respective target sinograms and the filtered sinograms corresponding to the input sinograms.

12. The apparatus according to claim 10, wherein the circuitry is further configured to filter the one of the input sinograms using the filter, wherein the filter is an adaptive filter in which the convolution kernel varies as a function of position within the one of the input sinograms thereby adapting to features represented in the one of the input sinograms.

13. A method, comprising:
obtaining radiation data representing an intensity of radiation detected at a plurality of detectors;
acquiring a neural network having weighting coefficients that have been trained to determine parameters of a filter in response to an input, the parameters defining a shape function of a convolution kernel of the filter;
applying the radiation data to the neural network, and in response outputting the parameters of the filter based on the radiation data;
denoising the radiation data by applying the filter defined by the output parameters from the neural network to generate filtered radiation data, and
reconstructing an image from the filtered radiation data.

14. The method according to claim 13, wherein obtaining the radiation data includes that the radiation data is a sinogram acquired by generating X-ray projection images at a series of projection views in which an angle between an X-ray source and the plurality of detectors is rotated relative to an image subject, and denoising the sinogram by applying the filter defined by the output parameters from the neural network generates a filtered sinogram, wherein the filter is applied to a three-dimensional volume of the sinogram or to two-dimensional slices of the sinogram, which include a segment dimension and a channel dimension, a view dimension and the channel dimension, and/or the segment dimension and a view dimension.

15. The method according to claim 13, wherein obtaining the radiation data includes that the radiation data is one of X-ray computed tomography (CT) data, X-ray fluoroscopy data, gamma-ray positron emission tomography (PET), and single-photon emission CT data (SPECT).

16. The method according to claim 13, wherein denoising the radiation data by applying the filter further includes that the shape function of the filter is a multi-variate, low-pass-filter kernel and the parameters of the filter comprise values defining widths and an orientation of the multi-variate, low-pass-filter kernel, and the values comprising the parameters vary as a function of pixel position within the radiation data.

17. The method according to claim 14, wherein acquiring the neural network further includes that the weighting coefficients have been trained using training data including input data and target data, the input data comprising first training sinograms acquired using a first radiation dose, and the target data comprising second training sinograms acquired using a second radiation dose that is greater than the first radiation dose.

18. The method according to claim 14, further comprising
obtaining a training dataset comprising input sinograms paired with respective target sinograms, the input sinograms exhibiting greater noise than the corresponding target sinograms in the respective pairs,
using the neural network to filter one of the input sinograms by
applying the one of the input sinograms to the neural network and in response outputting parameters of the filter, and
denoising the one of the input sinograms by applying, to the one of the input sinograms, the filter defined by the parameters output from the neural network, and thereby generating a denoisfiltered sinogram, and
training the neural network iteratively adjusting the weighting coefficients to minimize a value of a loss function, the loss function measuring a disagreement between the respective target sinograms and the denoised sinograms corresponding to the input sinograms.

19. The method according to claim 18, wherein denoising the one of the input sinograms using the filter further includes that the filter is an adaptive filter in which the convolution kernel varies as a function of position within the one of the input sinograms thereby adapting to features represented in the one of the input sinograms.

20. A non-transitory computer-readable storage medium including executable instructions, which when executed by circuitry, cause the circuitry to perform the method according to claim 13.

21. The apparatus according to claim 1, wherein the circuitry is configured to apply the radiation data to the neural network, and in response outputting the parameters changed for each position of the radiation data.

* * * * *